United States Patent [19]

Shum et al.

[11] Patent Number: 4,522,934
[45] Date of Patent: Jun. 11, 1985

[54] VANADOTUNGSTOMOLYBDOPHOSPHORIC ACID OXIDATION CATALYST

[75] Inventors: Wilfred P. Shum, East Windsor; John F. White, Princeton, both of N.J.; Eva M. Beals, Washington Crossing, Pa.

[73] Assignee: Atlantic Richfield Company, Los Angeles, Calif.

[21] Appl. No.: 468,810

[22] Filed: Feb. 22, 1983

Related U.S. Application Data

[62] Division of Ser. No. 258,102, Apr. 27, 1981, abandoned.

[51] Int. Cl.$^3$ .......................... B01J 27/14; C07B 3/00
[52] U.S. Cl. .................................. 502/209; 502/210; 502/211; 562/599
[58] Field of Search ............................... 252/435, 437

[56] References Cited

U.S. PATENT DOCUMENTS

| | | | |
|---|---|---|---|
| 4,146,574 | 3/1979 | Onoda et al. | 423/299 |
| 4,192,951 | 3/1980 | Slinkard et al. | 252/437 X |
| 4,268,448 | 5/1981 | Franz et al. | 252/437 X |
| 4,272,408 | 6/1981 | Daniel | 252/437 |
| 4,273,676 | 6/1981 | Motsumoto et al. | 252/437 X |
| 4,320,227 | 3/1982 | Motsumoto et al. | 252/437 X |
| 4,335,018 | 6/1982 | Franz et al. | 252/435 |

FOREIGN PATENT DOCUMENTS

| | | | |
|---|---|---|---|
| 0031729 | 7/1981 | European Pat. Off. | 252/437 |
| 47-30515 | 8/1972 | Japan | 252/437 |
| 2045635 | 11/1980 | United Kingdom | 252/437 |

OTHER PUBLICATIONS

PNMR, Studies on Molybdic and Tungstic Heteropolyanions Massart et al., Mar. 3, 1977, Inorganic Chemistry.

Primary Examiner—William G. Wright
Attorney, Agent, or Firm—Michael S. Jarosz

[57] ABSTRACT

A novel synthetic procedure is disclosed for producing heteropolyacid catalysts having the general formula $H_{3+x}PV_xW_{3-x}Mo_9O_{40}$ where $0<x<3$. The synthesis of these catalysts requires the formation of a defect structure wherein three of the twelve transition metals which surround the phosphorus hetero atom are missing. Three metal atoms of two other transition metals are then added to the cluster in a separate step by mixing $Na_3H_6PMo_9O_{34}$ with the oxides of such transition metals in the presence of hydrochloric acid. A preferred catalyst having the formula $H_{3.5}PV_{0.5}W_{2.5}Mo_9O_{40}$ is also described.

4 Claims, 1 Drawing Figure

VANADOTUNGSTOMOLYBDOPHOSPHORIC ACID OXIDATION CATALYST

CROSS-REFERENCE TO RELATED PATENT APPLICATIONS

This is a divisional of application Ser. No. 258,102 filed Apr. 27, 1981 now abandoned.

The present application is related to U.S. patent application Ser. No. 257,675, filed of even date, entitled "Oxidation of Isobutylene Oxide To Methacrylic Acid And Methacrolein", and to application Ser. No. 258,101 filed of even date, entitled "High Selectivity Process For Vapor Phase Oxydehydrogenation Of Alkanoic Acids, Such As Isobutyric Acid, Using Dawson Structure Phosphomolybdic Acid", which applications are assigned to the assignee of the present application, and which are hereby incorporated by reference as if fully set forth herein.

BACKGROUND OF THE INVENTION

The present invention relates to the field of heteropoly acids, and more particularly those heteropoly acids which comprise vanadium, tungsten, phosphorous and/or molybdenum.

Heteropolyacids are a recognized class of acids containing large amounts of oxygen and hydrogen, and multiple atoms of one or more elements, such as molybdenum or tungsten, surrounding one or more heteroatoms of another element, such as phosphorous. Polyanions of such acids consist primarily of octahedral $MoO_6$ or $WO_6$ groups, so that the conversion of $[MoO_4]^{2-}$ or $[WO_4]^{2-}$ into polyanions requires an increase in coordination number. Cotton and Wilkinson, "Advanced Inorganic Chemistry", 4th ed., pp. 852–861, Wiley & Sons, N.Y. (1980) disclose that heteropolyanions can be formed either by acidification of solutions containing the requisite simple anions, or by introduction of the hetero element after first acidifying the molybdate or tungstate. As indicated at Table 22-C-2 of Cotton and Wilkinson (pg. 857), various heteropolyanion formula types are known.

Heteropolyacids such as molybdophosphoric acids, are known to exist in the stoichiometry of the "Keggin" structure ($PMo_{12}O_{40}^{3-}$), as well as in the stoichiometry of a Dawson structure ($P_2Mo_{18}O_{62}^{6-}$). Of these structures, the "Keggin" structure is the most commonly formed cluster, and Keggin structure molybdophosphoric acids are known to be suitable vapor phase catalysts in the oxidative dehydrogenation of isobutyric acid to methacrylic acid. In Japanese Patent Disclosure No. 1975-4014 dated Jan. 16, 1975 entitled "A Process for Manufacturing Methacrylic Acid, abstracted at *Chemical Abstracts*, Volume 83, 4408b (1975), the use of molybdophosphoric acid having the empirical formula $H_3Mo_{12}PO_{40}·nH_2O$, as well as molybdovanadophosphoric acid, are disclosed for use in vapor phase oxidative dehydrogenations of isobutyric acid. Such reactions are performed in the presence of oxygen and other gases such as nitrogen, steam, etc., such reactions being carried out in the temperature range of 200°–400° C., preferably 250°–350° C. More particularly, this Japanese patent disclosure indicates that the selectivity of methacrylic acid can be improved by using a catalyst which is prepared by adding a sulfate of an alkali metal, nickel or cobalt to a heteropolyacid.

It has long been known to use various heteropolyacids to catalyst certain organic reactions. For example, in U.S. Pat. No. 4,192,951, vapor phase oxidation procedures are disclosed utilizing various heteropolyacid catalysts, including heteropolymolybdic catalysts containing vanadium, tungsten, tantalum or niobium. Such compounds act as catalysts for the synthesis of materials such as maleic acid and acetic acid. U.S. Pat. No. 4,192,951, also discloses a molybdophosphoric acid catalyst having an empirical formula of $H_6[P_2Mo_{18}O_{62}]$ which was prepared using a procedure involving the refluxing of $Mo_3$ and $H_3PO_4$ overnight to produce a bright yellow filtrate. Although the empirical formula provided relating to the molybdophosphoric acid catalyst of the '951 disclosure corresponds to the empirical formula of a Dawson structure catalyst, no mention is made in the '951 patent of the stoichiometry of the structure obtained in Example 1. It is clear from the filtrate color reported in the '951 patent that the stoichiometry of the '951 catalyst is not of the "Dawson" type. In an article entitled "Contribution To The Chemistry of Phosphomolybdic Acids, Phosphotungstic Acids, and Allied Substances", by Hsein Wu, *J. Biol. Chem.*, 43, 189 (1920) a proper procedure for preparing phospho-18-molybdic acid of the Dawson structure is disclosed. As explained by Wu at pages 196 and 197, care must be taken during the preparation of such an acid to avoid the formation of yellow crystals and to obtain orange crystals which are indicative of phospho-18-molybdic acid of the Dawson structure.

One approach to the preparation of heteropolyanions is the formation of compounds with a Keggin-defect structure which are derived from an alpha-$PM_{12}$ structure by removing one $MO_6$ octahedron or three $MO_6$ octahedra of the same ($M_3$) set. See "P-NMR Studies on Molybdic and Tungstic Heteropolyanions: Correlation Between Structure and Chemical Shift", Massart et al, *Inorganic Chemistry*, 16, 2916–2921 (1977). Massart discloses that metal atoms, other than tungsten can partly or wholly fill these holes, giving rise to such compounds as $PW_9Mo_3$, $PW_{10}Mo_2$, or $PW_{11}Mo$. In particular, Massart discloses the synthesis of various molybdotungstophosphoric acids wherein holes in the defect structure are filled with atoms of a given metal, such as molybdenum. As a result, Massart discloses compounds having up to two transition metals in a heteropolyanion structure.

In U.S. Pat. No. 4,146,574 (Onoda et al) entitled "Process for Preparing Heteropoly-acids", certain heteropolyacid catalysts are disclosed as being useful in oxidations and oxidative dehydrogenations, as for example, the oxidative dehydrogenation of isobutyric acid to methacrylic acid, and the oxidative dehydrogenation of isobutyraldehyde to methacrolein and methacrylic acid. (See columns 7 and 8, and particularly Tables III and V). The heteropolyacids of U.S. Pat. No. 4,146,574 are indicated as being represented by the general formula:

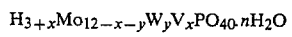

wherein x is an integer of 1 to 4, y is an interger of 0 to 3, the sum of x+y is 1 to 4, and n represents a number for the water of crystallization and usually has a value within the range of 16 to 32 in the crystalline state. Although this formula may be considered to disclose a vanadotungstomolybdophosphoric heteropoly acid, U.S. Pat. No. 4,146,574 provides no example of such a heteropolyacid. Further, as described hereinafter, applicants have found that the synthetic procedure set forth in the Onoda patent will not result in the incorporation of tungsten in a vanadomolybdophosphoric acid.

While the above-described methods for converting isobutyric acid to methacrylic acid have achieved some success, a need still exists for methods for efficiently and selectively converting isobutyric acid to methacrylic acid.

SUMMARY OF THE INVENTION

The present invention provides a novel synthetic procedure for producing vanadotungstomolybdophosphoric acid having the general formula:

$H_{3+x}PV_xW_{3-x}Mo_9O_{40}$, where $0<x<3$.

This method involves the preparation of a Keggin-defect-structure of phosphomolybdic acid and the subsequent addition of 3 atoms of at least 2 different metals into that defect structure to produce the desired vanadotungstomolybdophosphoric acid oxidation catalyst. By varying the molar ratio of metals to be added to the phosphomolybdic acid defect structure, reaction products are obtained which are useful as oxidation catalysts. More particularly, by varying the ratios of tungsten and vanadium oxides incorporated into this defect structure, optimal reaction products may be obtained for use in catalyzing certain syntheses, such as the synthesis of certain alpha-beta unsaturated carbonyl compounds. For example, the herein disclosed $H_{3.5}PV_{.5}W_{2.5}Mo_9O_{40}$ catalyst is quite useful in the oxydehydrogenation of isobutyric acid (IBA) to methacrylic acid (MAA) with a selectivity of 77%. This selectivity compares favorably to the 70% selectivity reported in U.S. Pat. No. 4,146,574 when $H_5PV_2Mo_{10}O_{40}$ is used as a catalyst.

Accordingly, the primary object of the present invention is the provision of a novel method for synthesizing vanadotungstomolybdophosphoric acid catalysts.

A further object of the present invention is the provision of novel vanadotungstomolybdophosphoric acid catalysts.

A further object of the present invention is the provision of novel processees using the aforementioned catalysts.

These and other objects of the present invention will become apparent from the following more detailed description.

DESCRIPTION OF THE PREFERRED EMBODIMENT

Figure 1:
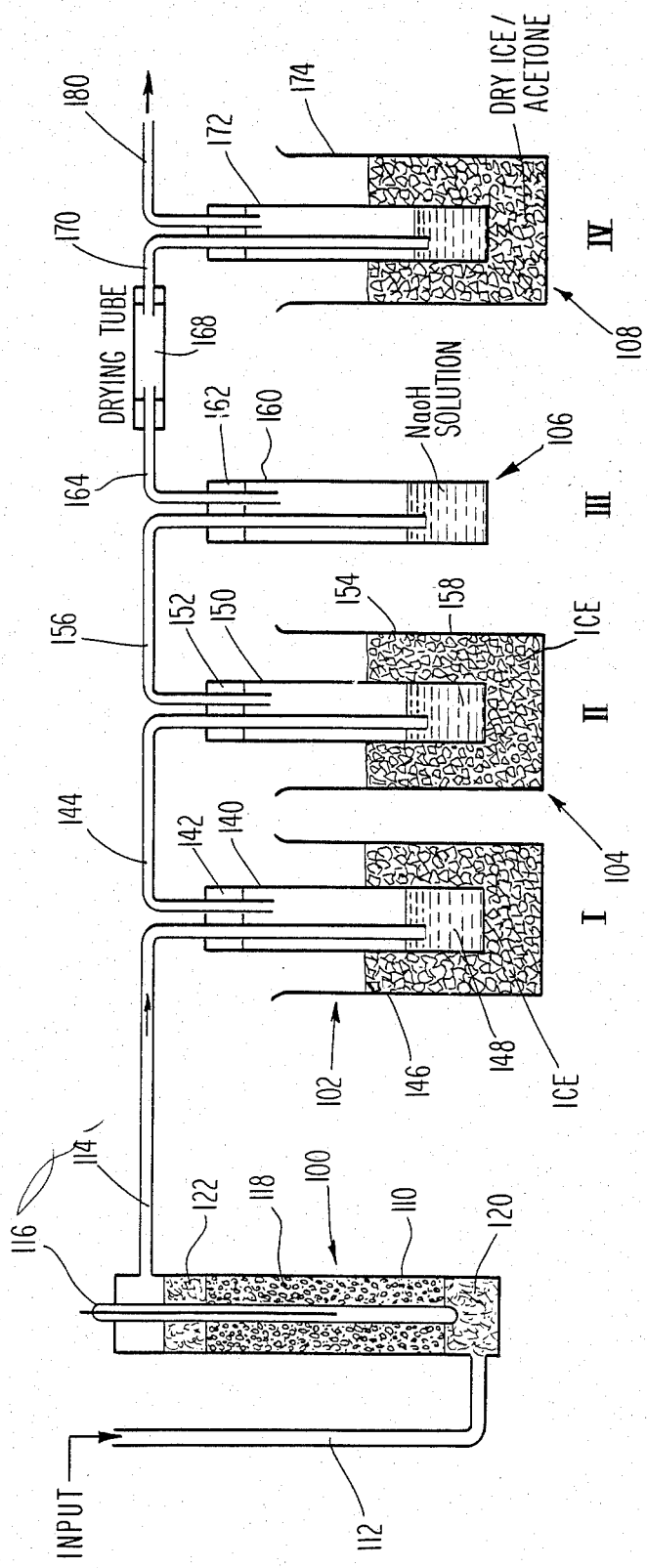
FIG. 1 is a diagram of the preferred embodiment laboratory scale apparatus used in demonstrating the catalytic activity of the disclosed vanadotungstomolybdophosphoric acid oxidation catalyst.

While particular examples are referred to in the following description for the purposes of illustration, one of ordinary skill in the art will recognize that various modifications can be made to the materials and methods described herein without departing from the scope of the present invention which is defined more particularly in the appended claims.

The present invention provides a method for synthesizing vanadotungstomolybdophosphoric acid catalysts of the general formula:

$H_{3+x}PV_xW_{3-x}Mo_9O_{40}$, where $0<x<3$.

In accordance with the method of the present invention, a heteropolyacid, such as a salt of molybdophosphoric acid ($Na_3H_6PMo_9O_{34}$) is first prepared, having a Keggin defect structure wherein 3 of the 12 transition metals surrounding the phosphorus heteroatom are missing. This defect structure salt is preferably prepared in accordance with the teachings of R. Massart, et al, *Inorganic Chemistry*, 16, 2916 (1977) which is hereby incorporated by reference. Next, transition metal atoms of two different metals are added to this defect cluster in a separate step by mixing the aforementioned $Na_3H_6$-$PMo_9O_{34}$ with the oxides of those different metals in the presence of hydrochloric acid. Preferably the combined tungsten and vanadium are incorporated in this molybdophosphoric defect structure to produce a vanadotungstomolybdophosphoric acid catalyst exhibiting a catalytic activity and selectivity which differs from those of the vanadomolybdophosphoric acid or tungstomolybdophosphoric acid catalysts heretofore known to the art.

One vanadotungstomolybdophosphoric acid catalyst produced in accordance with the present invention has been found to be more selective than vanadomolybdophosphoric acid in converting isobutyric acid to methacrylic acid (See U.S. Pat. No. 4,146,574). It is thus anticipated that these and other catalysts in accordance with the present invention will also be useful as catalysts for the oxidation of methacrolein to methacrylic acid, the oxidation to acrolein to acrylic acid, and the oxidation of butane/butene to maleic anhydride.

Since U.S. Pat. No. 4,146,574 discloses that the mixing of metal oxides in a desired stoichiometry, heating, filtering off the undissolved oxides and impregnating a catalyst support with the aqueous solution of the heteropolyacid will result in a catalyst incorporating each of the mixed metal oxides, an attempt was made to produce a vanadotungstomolybdophosphoric acid catalyst using the procedures of that patent. Accordingly, 9 grams of an 85% solution of $H_3PO_4$(0.07806 moles P) were mixed with 100 grams of $MoO_3$ (0.6947 moles Mo), 7.02 grams of $V_2O_5$ (0.07719 moles V) and 35.80 grams of $WO_3$ (0.1544 moles W). This mixture was suspended in 700 ml. of water in a 1000 ml. round bottom flask, and refluxed for 24 hours with continuous stirring to yield an orange red solution. The insolubles were then filtered off and the clear orange red filtrate evaporated at 80° C.; the red crystalline solid was filtered and air dried. The product could be redissolved in water yielding a clear orange red solution. Elemental analysis of this material disclosed it to have 1.53% hydrogen, 1.8% phosphorous 2.97% vanadium, 51.48% molybdinum, and "none or trace" tungsten. Accordingly, it was concluded that tungsten may not be incorporated into a vanadomolybdophosphoric acid structure by using the method of the '574 patent.

In accordance with the method of the present invention a heteropolyacid catalyst of the structure $H_{3.5}PV_{.5}W_{2.5}Mo_9O_{40}$ was prepared by preparing $Na_3H_6PMo_9O_{34}$ in accordance with the aforementioned procedure of Massart. Sodium phosphate $Na_2HPO_4.12H_2O$(18 grams) was dissolved in a mixture of 70% aqueous perchloric acid (73 mls.) and water (20 ml.). The solution was cooled to −10° C. A solution of sodium molybdate $Na_2MoO_4.3H_2O$(108 grams) in water (200 ml.) was then added dropwise to the above solution at −10° C.; the resulting solution was pale yellow. The sodium salt that precipitated out after standing overnight at 0° C. was filtered and air dried. Na$_3$H$_6$PMo$_9$O$_{34}$.13H$_2$O (30 grams, 0.018 mole) was added to a 100 ml. aqueous solution of Na$_2$WO$_4$ (12 mgs., 0.036 mole) and NaVO$_3$ (2.9 grams, 0.018 mole) with vigorous stirring. After mixing the solution with 30 ml. of concentrated hydrochloric acid, the heteropolyacid solution was extracted with an equal volume of diethyl ether. The dark red ethereal extract was collected and diluted with an equal volume of distilled water. The ether was removed by warming the solution on a hot plate. The orange crystalline product obtained after evaporation was filtered and air dried.

A silica supported catalyst was then prepared by dissolving 15 grams of the vanadotungstomolybdophosphoric acid in 5 grams of distilled water to give a clear, dark orange solution. With stirring, 2.5 grams of Celite ® 408 (20–50 mesh size) silica was added to yield a thick slurry. The impregnated catalyst was calcined at 280° C. for 2 hours in an automatic furnace with a constant flow of air. Finally, the 20-50 mesh size calcined catalyst was separated out using a sieve shaker.

The aforementioned vanadotungstomolybdophosphoric acid was subjected to infrared spectroscopy (with peaks at 1060, 960, 890, and 790 cm$^{-1}$) which confirmed that the heteropolyacid obtained after ether extraction possesses the Keggin cluster structure. Although the molar proportion used above would theoretically result in a compound having the formula H$_4$PVW$_2$Mo$_9$O$_{40}$, elemental analysis indicates that the material obtained is best represented by the formula H$_{3.5}$PV$_{.5}$W$_{2.5}$Mo$_9$O$_{40}$. It is thus theorized that this procedure favors the incorporation of tungsten over vanadium into the heteropolyacid product. It is theorized that the abovedescribed product may constitute a mixture of heteropolyacids comprising major amounts of H$_3$PW$_3$Mo$_9$O$_{40}$ and H$_4$PVW$_2$Mo$_9$O$_{40}$ relatively lesser amounts of H$_5$PV$_2$W$_1$Mo$_9$O$_{40}$ and little if any H$_6$PV$_3$Mo$_9$O$_{40}$. Although the process for incorporating vanadium and tungsten into a phosphomolybdic structure is not fully understood, it is currently anticipated that variations in the amounts of the vanadium and tungsten oxides used in this process may be used to derive all heteropolyacid reaction products in accordance with the following formula:

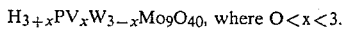

H$_{3+x}$PV$_x$W$_{3-x}$Mo$_9$O$_{40}$, where 0<x<3.

In order to test the catalytic activity of the abovedescribed products, oxydehydrogenations of isobutyric acid to methacrylic acid were conducted. These oxydehydrogenations were conducted in the laboratory scale apparatus illustrated in FIG. 1. This apparatus comprises a reactor designated generally 100 and a series of collection traps designated generally 102, 104, 106 and 108. Reactor 100 comprises a glass reactor vessel 110 which is fed through side arm 112 and which exhausts through output conduit 114. This reactor is fitted with an axially disposed thermometer well 116. Reactor vessel 110 contains a catalyst bed 118 located within the reactor flow stream between glass bead packings 120 and 122. In a preferred embodiment, the catalyst bed comprises 50% heteropoly acid deposited on a suitable silica substrate, such as Celite ® 408 resin which is sold by the JohnsManville Company, Filtration & Minerals Division, Denver, CO 80217. During use, the reactor is submerged in a salt bath (not shown) filled with 60% ZnCl$_2$, 20% NaCl, and 20% KCl, heated to the desired temperatures. An Isco pump model 314 was used to feed a premixed aqueous isobutyric acid solution to a pre-heater where the liquid feed was vaporized and passed on to the catalyst bed. Oxygen and nitrogen were simultaneously fed into the reactor using a flow meter, model 10A1460, which may be obtained from Fisher and Porter.

The reaction products produced in reactor 100 were collected in the recovery train comprising traps 102, 104, 106 and 108. Condensation trap 102 comprises collection vessel 140 containing a dual port stopper 142 for receiving conduit 114 and tube 144 which are journaled therethrough. Collection vessel 140 is partially immersed in ice contained within beaker 146. Reaction products 148 are thus collected by condensation within collecting vessel 140. Those products which do not condense as liquids within reaction vessel 140 are passed through tube 144 to collection trap 104, which similarly comprises collection vessel 150, stopper 152 and ice water container 154 for further fascilitating the collection of condensed reaction products 158.

As shown in FIG. 1, gaseous products not collected in trap 104 pass through conduit 156 to carbon dioxide collection trap 106. Carbon dioxide collection trap 106 similarly comprises a collection vessel 160 fitted with a dual apertured rubber stopper 162. Collection vessel 160 contains a sodium hydroxide solution for collecting carbon dioxide, the amount of which can be subsequently determined by back titrating with an acid. After passing through output tube 164 to a drying tube 168 for removing water vapor from the process stream, the stream is fed through input tube 170 to the collection vessel 172 of volatile products trap 108. Volatile products trap 108 further comprises a container 174 which holds a dry ice/acetone bath in which at least a portion of collection vessel 172 is immersed. The process stream is then vented through exhaust tube 180.

Total acids (isobutyric acid, acetic acid and methacrylic acid) recovered from traps 1 and 2 were then determined by titrating the aqueous solutions with 0.10M NaOH using phenolphthalein as the indicator. As mentioned above, carbon dioxide collected in trap III (106) was determined by back titration as with 0.10N HCl. The reaction products collected by traps 1 and 2 were further subjected to gas chromatographic analysis to determine percent conversion and, where appropriate, the percent selectivity of the reaction. Gas chromatographic analysis was also used to determine carbon dioxide, oxygen, and, where appropriate, carbon monoxide, using N$_2$ as the standard.

As used herein, percent conversion equals the moles of isobutyric acid reacted divided by the moles of isobutyric acid supplied times 100. As used herein, percent selectivity refers to the number of moles of a methacrylic acid end product recovered divided by the number of moles of isobutyric acid starting material reacted, times 100.

The novel catalysts of the present invention are particularly suited for vapor phase syntheses of alpha-beta unsaturated carbonyl compounds from corresponding saturated substrates having at least one hydrogen atom bonded to each of the alpha and beta carbon atoms of those substrates. These substrates are preferably branched at the alpha position, with each branch comprising up to five carbon atoms. Carboxylic acids are particularly suited as substrates for these syntheses, however esters, ketones, and less preferably aldehydes, may also be used as such substrates. Such preferred esters include methyl, ethyl, propyl butyl and pentyl esters of said compounds. Such preferred ketones include ketones having a second hydro-carbyl group comprising one to five carbon atoms attached thereto. Of these compounds, isobutyric acid is a preferred representative substrate which is convertable to methacrylic acid. Propanoic acid conversions to acrylic acid are also preferred.

Using catalysts supported on Celite ®408 silica, as referred to above, oxydehydrogenations of isobutyric acid were conducted and isobutyric acid conversion and methacrylic acid selectivities were determined. The results for various vanadomolybdophosphoric, vanadotungstophosphoric and tungstomolybdophosphoric acids are set forth in Table I:

TABLE I

Oxidative Dehydrogenation of Isobutyric Acid (IBA) to Methacrylic Acid (MAA)

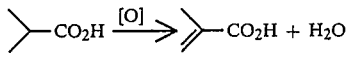

IBA/$H_2O$/$O_2$/$N_2$ = 1/2/6/24 (moles)
50% heteropolyacid/Celite 408
contact time = 1 second
bath temperature = 280° C.
sample collection time = 2–3 hours

| Run # | Catalyst | % IBA | % MAA | % Acetone | % HOAc | % $CO_2$ | % CO | % Carbon Balance | % Selectivity To MAA |
|---|---|---|---|---|---|---|---|---|---|
| 83-78 | $H_4PVMo_{11}O_{40}$/Celite 408 | 15% (14%) | 62% (58%) | 11% | 0% | 6% | 12% | 106% (100%) | 73% (68%) |
| 83-80 | $H_4PVMo_{11}O_{40}$/Celite 408 | 11% (12%) | 56% (58%) | 12% | 1% | 5% | 9% | 96% (100%) | 63% (66%) |
| 83-82 | $H_4PVMo_{11}O_{40}$/Celite 408 | 15% (14%) | 59% (57%) | 12% | 1% | 6% | 9% | 103% (100%) | 69% (66%) |
| 83-86 | $H_4PVMo_{11}O_{40}$/Celite 408 | 13% (13%) | 63% (61%) | 13% | 1% | 4% | 7% | 102% (100%) | 72% (70%) |
| 83-88 | $H_4PVMo_{11}O_{40}$/Celite 408 | 18% (18%) | 56% (55%) | 11% | 1% | 5% | 10% | 102% (100%) | 69% (67%) |
| 83-92 | $H_6PV_3Mo_9O_{40}$/Celite 408 | 14% (14%) | 58% (57%) | 13% | 1% | 5% | 10% | 101% (100%) | 67% (66%) |
| 83-94 | $H_6PV_3Mo_9O_{40}$/Celite 408 | 18% (17%) | 58% (55%) | 13% | 1% | 6% | 10% | 104% (100%) | 69% (67%) |
| 83-96 | $H_6PV_3Mo_9O_{40}$/Celite 408 | 18% (17%) | 58% (56%) | 14% | 1% | 5% | 9% | 104% (100%) | 71% (68%) |
| 83-98 | $H_6PV_3Mo_9O_{40}$/Celite 408 | 20% (19%) | 55% (53%) | 14% | 1% | 5% | 9% | 103% (100%) | 68% (66%) |
| 83-70 | $H_5PV_2W_{10}O_{40}$/Celite 408 | 72% (79%) | 3% (3%) | 2% | 0 | 3% | 10% | 90% (100%) | 10% (15%) |
| 83-76 | $H_5PV_2W_{10}O_{40}$/Celite 408 | 81% (80%) | 3% (3%) | 2% | 0 | 4% | 12% | 102% (100%) | 13% (12%) |
| 83-102 | $H_3PW_3Mo_9O_{40}$/Celite 408 | 66% (61%) | 24% (19%) | 6% | 0 | 4% | 10% | 109% (100%) | 70% (60%) |
| 83-104 | $H_3PW_3Mo_9O_{40}$/Celite 408 | 72% (69%) | 19% (19%) | 4% | 0 | 3% | 7% | 104% (100%) | 68% (60%) |
| 83-48 | $H_5PV_2Mo_{10}O_{40}$/Celite 408 | 14% | 61% | 14% | 1% | 5% | 4% | 100% | 71% |
| 83-50 | $H_5PV_2Mo_{10}O_{40}$/Celite 408 | 12% | 58% | 12% | 1% | 4% | 6% | 100% | 70% |
| 83-52 | $H_5PV_2Mo_{10}O_{40}$/Celite 408 | 19% | 57% | 13% | 1% | 4% | 5% | 100% | 70% |

NOTE:
Normalized data are bracketed below the actual experimental data. All %'s are percents of the carbon content of the reacted substrate.

For purposes of comparison, the vanadotungstomolybdophosphoric acid prepared as described above was run under the same reaction conditions to produce comparative data. The results of these experiments are set forth in Table II.

TABLE II

Oxidative Dehydrogenation of Isobutyric Acid (IBA) to Methacrylic Acid (MAA)

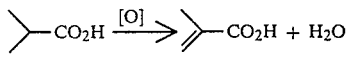

IBA/$H_2O$/$O_2$/$N_2$ = 1/2/6/24 (moles)
50% $H_{3.5}PV_{.5}W_{2.5}Mo_9O_{40}$/Celite 408
contact time = 1 second
bath temperature = 280° C.
sample collection time = 2–3 hours

| Run # | % IBA | % MAA | % Acetone | % HOAc | % $CO_2$ | % CO | % Carbon Balance | % Selectivity To MAA |
|---|---|---|---|---|---|---|---|---|
| 90-52 | 45% (48%) | 39% (39%) | 9% | 1% | 2% | 1% | 94% (100%) | 68% (76%) |
| 90-54 | 47% (50%) | 35% (37%) | 9% | <1% | 2% | 1% | 94% (100%) | 65% (73%) |
| 90-56 | 51% | 34% | 11% | 1% | 2% | 1% | 100% | 71% |
| 90-58 | 54% | 33% | 7% | 1% | 2% | <1% | 96% | 71% |

TABLE II-continued
Oxidative Dehydrogenation of Isobutyric Acid (IBA) to Methacrylic Acid (MAA)

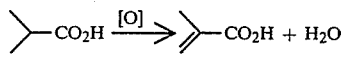

IBA/H$_2$O/O$_2$/N$_2$ = 1/2/6/24 (moles)
50% H$_{3.5}$PV$_{.5}$W$_{2.5}$Mo$_9$O$_{40}$/Celite 408
contact time = 1 second
bath temperature = 280° C.
sample collection time = 2-3 hours

| Run # | % IBA | % MAA | % Acetone | % HOAc | % CO$_2$ | % CO | % Carbon Balance | % Selectivity To MAA |
|---|---|---|---|---|---|---|---|---|
| | (56%) | (34%) | | | | | (100%) | (78%) |
| 90-62 | 45% | 35% | 8% | <1% | 2% | 1% | 92% | 64% |
| | (49%) | (38%) | | | | | (100%) | (75%) |

NOTE:
Normalized data are bracketed below the actual experimental data. All percents are percents of the carbon content of the substrate.

By comparing the results set forth in Tables I and II above, it will be noted that the vanadomolybdophosphoric acid catalyst tested shows conversion percentages in the 80-89% range, and selectivities of between 63-73%, or normalized to about 66-70%. As listed in Table I, testing has indicated that H$_5$PV$_2$Mo$_{10}$O$_{40}$ produces isobutyric acid conversions of about 85% with a selectivity of about 70%. Results for these and other catalyst are summarized in Table III:

TABLE III

| Catalyst (50% HPA/Celite 408) | IBA Conversion | MAA Selectivity |
|---|---|---|
| H$_4$PVMo$_{11}$O$_{40}$ | 86% | 67% |
| H$_5$PV$_2$Mo$_{10}$O$_{40}$ | 85% | 70% |
| H$_6$PV$_3$Mo$_9$O$_{40}$ | 83% | 67% |
| H$_7$PV$_4$Mo$_8$O$_{40}$ | 58% | 61% |
| H$_5$PV$_2$W$_{10}$O$_{40}$ | 20% | 14% |
| H$_3$PW$_3$Mo$_9$O$_{40}$ | 35% | 58% |
| H$_3$PMo$_{12}$O$_{40}$ | 82% | 44% |
| H$_3$PW$_{12}$O$_{40}$ | inactive | |

NOTE:
Normalized to 100% carbon balance. All percents are percents of carbon content of substrate.

These results confirm the information reported in the aforementioned '574 patent indicating that H$_5$PV$_2$Mo$_{10}$O$_{40}$ has the best methacrylic acid selectivity of any vanadomolybdophosphoric acid catalyst reported.

In referring to Table II, it will be noted that the conversion percentage for isobutyric acid with one catalyst (H$_{3.5}$PV$_{.5}$W$_{2.5}$Mo$_9$O$_{40}$) was about 50% while the normalized carbon balance selectivities were in the range of 71 to 78, or about 74%.

The vanadotungstomolybdophosphoric acid product of the present invention is believed to be a more thermally stable catalyst than the 2-vanado-10-molybdophosphoric acid catalyst disclosed in the '574 patent. In the *Journal of the American Chemical Society*, 59, 1069 (1955) differential thermal analysis is reported as indicating that H$_3$PW$_{12}$O$_{40}$ is more thermally stable than H$_3$PMo$_{12}$O$_{40}$, the former decomposing at 600° C. and the latter at 400° C. It is, however, generally known that the selectivity of a heteropolyacid catalyst generally decreases as processing temperatures are increased. Nonetheless, tests were conducted to determine whether percentage conversions would increase without substantial losses in selectivity when oxydehydrogenations of isobutyric acid were conducted at higher temperatures. The results of these tests are set forth in Table IV:

TABLE IV
Oxidative Dehydrogenation of Isobutyric Acid (IBA) To Methacrylic Acid (MAA)

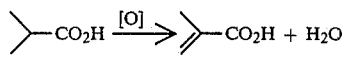

IBA/H$_2$O/O$_2$N$_2$ = 1/2/6/24 (moles)
50% H$_{3.5}$PV$_{.5}$W$_{2.5}$Mo$_9$O$_{40}$/Celite 408
contact time = 1 second
sample collection time = 2-3 hours

| Run # | Temp. | % IBA | % MAA | % Acetone | % HOAc | % CO$_2$ | % Carbon Balance | % Selectivity To MAA |
|---|---|---|---|---|---|---|---|---|
| 90-64 | 307° C. | 29% | 52% | 9% | 0% | 2% | 92% | 74% |
| | | (32%) | (57%) | | | | (100%) | (83%) |
| 90-80 | 300° C. | 24% | 58% | 8% | 1% | 5% | 96% | 76% |
| | | (25%) | (61%) | | | | (100%) | (81%) |
| 90-84 | 303° C. | 14% | 65% | 10% | 1% | 6% | 96% | 76% |
| | | (15%) | (68%) | | | | (100%) | (80%) |
| 90-86 | 301° C. | 16% | 60% | 12% | 1% | 5% | 94% | 72% |
| | | (17%) | (64%) | | | | (100%) | (77%) |
| 90-84 | 303° C. | 19% | 56% | 14% | 1% | 5% | 95% | 69% |
| | | (20%) | (59%) | | | | (100%) | (74%) |
| 90-106 | 317° C. | 7% | 74% | 12% | 2% | 6% | 101% | 79% |
| | | (7%) | (74%) | | | | (100%) | (79%) |

TABLE IV-continued
Oxidative Dehydrogenation of Isobutyric Acid (IBA) To Methacrylic Acid (MAA)

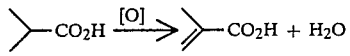

IBA/H$_2$O/O$_2$N$_2$ = 1/2/6/24 (moles)
50% H$_{3.5}$PV$_{.5}$W$_{2.5}$Mo$_9$O$_{40}$/Celite 408
contact time = 1 second
sample collection time = 2–3 hours

| Run # | Temp. | % IBA | % MAA | % Acetone | % HOAc | % CO$_2$ | % Carbon Balance | % Selectivity To MAA |
|---|---|---|---|---|---|---|---|---|
| 90-108 | 317° C. | 7% (7%) | 72% (68%) | 17% | 3% | 7% | 106% (100%) | 78% (73%) |
| 90-110 | 317° C. | 8% (8%) | 78% (74%) | 11% | 2% | 6% | 105% (100%) | 84% (80%) |

NOTE:
Normalized data are bracketed below the actual experimental data. All percents are percents of carbon content of substrate.

Quite surprisingly, using the vanadotungstomolybdophosphoric acid catalyst of the present invention, substantially higher conversions of isobutyric acid (up to about 93% at 317° C.) were obtained with selectivities for methacrylic acid ranging from 74 to 83%. As seen in Table IV, average IBA conversions of 78% with an MAA selectivity of 79% were obtained at 303° C. It may thus be concluded that the vanadotungstomolybdophosphoric acid catalyst of the present invention provides a superior method for performing vapor phase oxydehydrogenations of isobutyric acid to methacrylic acid.

It is not fully understood why the substitution of some molybdenum atoms with tungsten in a vanadomolybdophosphoric acid produces higher MAA selectivity. While not wishing to be limited to any specific theory, it is presently hypothesized that the specific orientation of the metal atoms within the Keggin cluster aids in the selectivity of the reaction due to the stereospecific nature of the synthesis involved and/or that the inherent properties of the tungsten atom introduced into the structure further enhance the selectivity of the reaction.

From the foregoing description, one of ordinary skill in the art will recognize that the reaction of the present invention should be conducted at sufficient temperatures to facilitate the conversion of the subject substrate to the desired end product(s), but below the temperature at which substantial decomposition of the subject catalyst occurs. For example, at atmospheric pressures, the temperature of the bath in which the catalyst is contained should be maintained between about 280°–350° C., and more preferably between 285°–335° C. Additionally, the subject reactions may be run at pressures between 5–50 psig, preferably 10–30 psig. It is also preferred to use an inert diluent gas to bring the system up to proper operating pressures and to otherwise maintain favorable reaction conditions. Such inert diluents include any gas which is otherwise inert to the system, including, for example, argon, helium, nitrogen, carbon dioxide and excess steam. In any event, the subject reactions should be run with enough steam to stabilize the catalyst by, for example, maintaining the hydration of the catalyst. Contact time of the substrate with the catalyst should be controlled to achieve optimum percentages of conversion at desired selectivities. Such contact times typically range between 0.1–10 seconds preferably between 0.5–5 seconds. In performing the subject reactions, sufficient oxygen should be introduced to accomplish the desired oxidation. Generally, 0.1–25, preferably 1–12, molar equivalents of oxygen per mole of substrate should be introduced with the substrate to carry out the subject oxidation. One of ordinary skill will further recognize that various catalyst supports other tnhan silica may be used with the disclosed catalyst. See for example, U.S. Pat. No. 4,146,574, column 3, lines 47–66, which patent is hereby incorporated by reference.

As seen from the above, a process is disclosed for producing a novel vanadotungstomolybdophosphoric acid catalyst. These catalysts are useful in catalyzing various vapor phase reactions, such as conversions of alpha-beta saturated carbonyl compounds to their alpha-beta unsaturated equivalents.

What is claimed is:

1. A method of preparing a three transition metal, Keggin structure heteropoly acid catalyst comprising the steps of:
   (a) providing a heteropolyacid Keggin defect structure of the formula: Na$_3$H$_6$PMo$_9$O$_{34}$ and
   (b) introducing into said defect structure transition metal oxides of vanadium and tungsten to produce a heteropolyacid product containing molybdenum, vanadium and tungsten metals in a Keggin structure.

2. The method of claim 1 wherein said oxides are introduced for incorporation into said defect structure in a molar ratio to vanadium of tungsten of about 1:2.

3. A heteropolyacid catalyst having the formula H$_{3+x}$PV$_x$W$_{3-x}$Mo$_9$O$_{40}$ wherein $0 < x < 3$, and wherein said heteropolyacid consists essentially of Keggin clusters.

4. The heteropolyacid of claim 3 wherein x is equal to about 0.5.

* * * * *